(12) United States Patent
Catterall et al.

(10) Patent No.: US 6,800,251 B2
(45) Date of Patent: Oct. 5, 2004

(54) SAMPLE HANDLING SYSTEM (75) Inventors: Clive Patrick Ashley Catterall, Worcestershire (GB); Duncan Edward Stephenson, Worcestershire (GB)

(73) Assignee: Malvern Instruments Limited (GB)

( * ) Notice: Subject to any disclaimer, the term of this patent is extended or adjusted under 35 U.S.C. 154(b) by 0 days.

(21) Appl. No.: 09/896,183

(22) Filed: Jun. 29, 2001

(65) Prior Publication Data

US 2002/0054834 A1 May 9, 2002

(30) Foreign Application Priority Data

Jul. 1, 2000 (GB) .............................................. 0016101
Feb. 13, 2001 (GB) .............................................. 0103432

(51) Int. Cl.[7] .............................................. G01N 21/84
(52) U.S. Cl. ..................... 422/99; 422/82.05; 422/102; 422/103; 436/164
(58) Field of Search .......................... 422/99, 102, 103, 422/82.05; 356/336, 337, 246; 436/177, 164

(56) References Cited

U.S. PATENT DOCUMENTS

| 5,351,118 A | * | 9/1994 | Spinell | .......................... 356/72 |
| 5,428,443 A | | 6/1995 | Kitamura et al. | ............ 356/336 |
| 5,439,288 A | | 8/1995 | Hoffman et al. | ............. 336/137 |

FOREIGN PATENT DOCUMENTS

| FR | 2716730 A1 | * 9/1995 | .......... G05D/16/16 |
| JP | 58163425 | 9/1983 | |
| WO | WO 0016888 | 3/2000 | |

OTHER PUBLICATIONS

Webster's Ninth New Collegiate Dictionary (Merriam Webster: Springfield, MA 1987), p. 503.*

* cited by examiner

*Primary Examiner*—Jan Ludlow
(74) *Attorney, Agent, or Firm*—Baker Botts LLP (57) ABSTRACT

A particle suspension handling system comprises a dispersion unit, a transport element, a cell and an outlet region. The dispersion unit has a transducer externally thereof, which is arranged, in use, to transfer energy into the suspension. The transport element is located within the dispersion unit. The transport element is arranged, in use, to recirculate the suspension about a flow path including the dispersion unit and the cell. The outlet region includes first and second valve members. The valve members can be arranged in a first configuration wherein they are spaced apart such that the space between them defines a discharge opening via which a fluid or the suspension exits the system, in use. The valve members can also be arranged in a second configuration wherein they abut and a flow path of substantially constant cross-section is provided about the outlet region.

22 Claims, 5 Drawing Sheets

Fig. 1

PRIOR ART

SAMPLE HANDLING SYSTEM

This invention relates to a sample handling system. More particularly it relates to a sample handling system wherein the sample is a fluid containing particles.

Large scale sample handling systems which are used in laser scattering particle characterisation apparatus typically contain 1 liter of dispersant in which a large amount of sample, typically 2.5–5 grams, is dispersed resulting in millions of particles being carried. The resulting suspension is then continually re-circulated from a storage reservoir to a measurement cell to allow measurement. As a result of the large number of particles the loss of a small percentage of particles from the measured sample by trapping at crevices, seals and by sedimentation does not significantly bias the results of the measurements.

However, as the volume of dispersant in the system decreases so does the number of particles that can be introduced into the system and the impact upon the particle characterisation measurements of losing even a small percentage of the particles is highly significant, as it is imperative that the portion of the sample presented to the laser beam must be representative of the sample as a whole. This is particularly important in that mechanisms for particle loss are size sensitive thus leading to a skewing of the measured particle size distribution.

A drive to miniaturise sample handling systems has arisen, principally from pharmaceutical drug discovery trials where the drug of interest may cost up to £100 k per gram. Therefore, only a small sample will be used in characterisation experiments and as high a recovery rate of the sample as possible is desirable.

Figure 1:
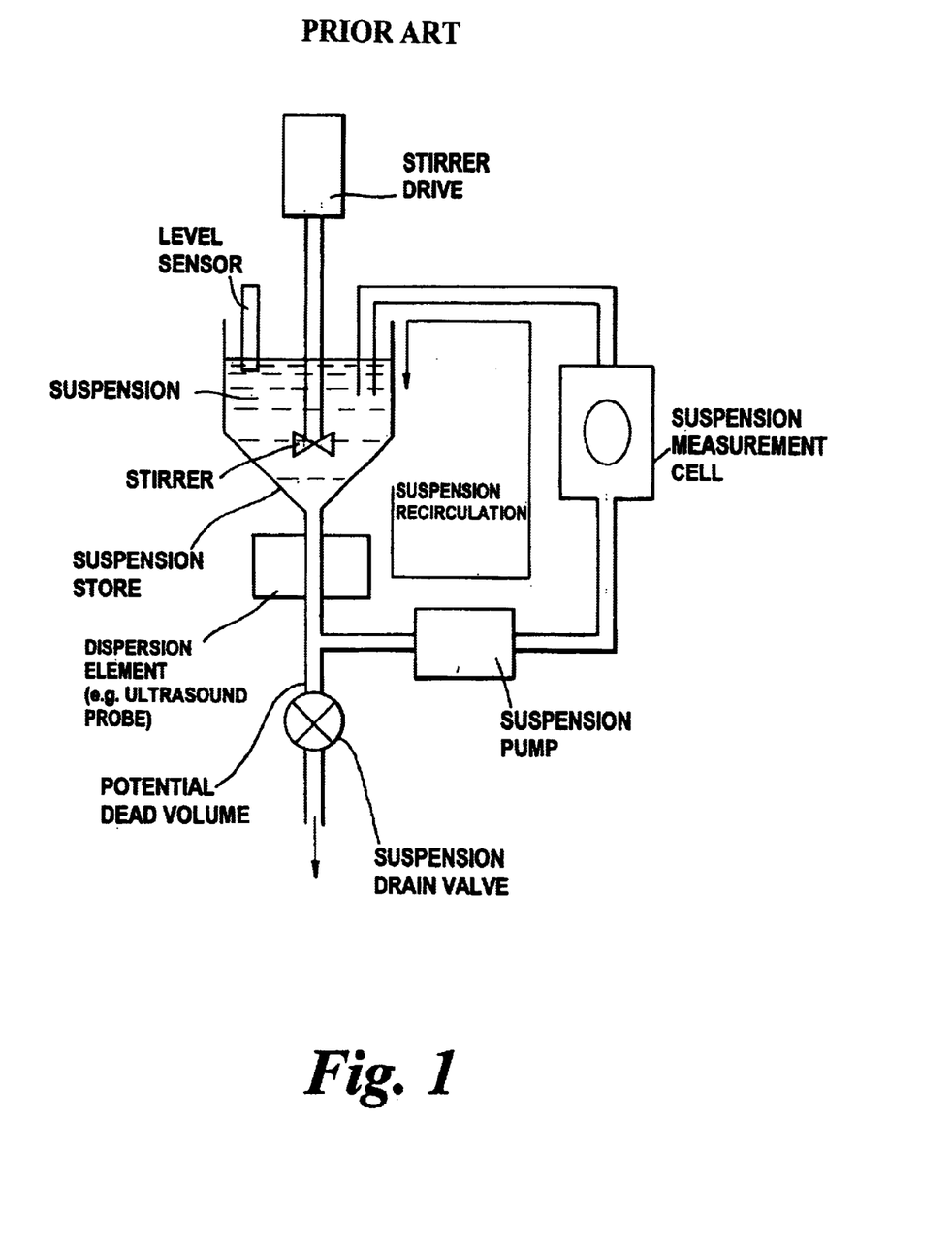
FIG. 1 is a schematic representation of the layout of a prior art, large volume sample handling system.

Another reason for miniaturisation is the use of exotic, expensive and possibly noxious dispersants, such as dimethyl sulphoxide (DMSO) or tetrahydrofuran (THF), which must be recovered after use. The significance of the dispersant is apparent when considering the "wash down" of the system. The system must be flushed up to 3 times after use in order to prevent cross contamination between measurement sets. Thus, for a 1 liter system up to 4 liters of dispersant must be used for each measurement set. It is therefore desirable to improve upon the basic features of large-scale sample handling systems (a schematic of which is shown in FIG. 1) whilst gaining additional benefits from the miniaturisation of the system.

Current small-scale sample handling systems have a total volume of approximately 150 ml per fill volume and use 0.2 to 0.5 grams of particles per sample. These sample handling systems have a number of further biases associated with them that can skew the measurement results including limitations upon the density of particles that can be measured as it requires a high pump power to keep heavy particles moving in a uniform random suspension. As particle size increases the volume increases as the cube of the particle diameter whereas the viscous drag forces, which maintain the particle in suspension, vary as the square of the diameter. Therefore, the particle size density drag force relationship is very important, for example 100 $\mu$m silicon particles will typically settle from suspension in water in a second, thereby severely limiting the available data acquisition period.

Figure 2:
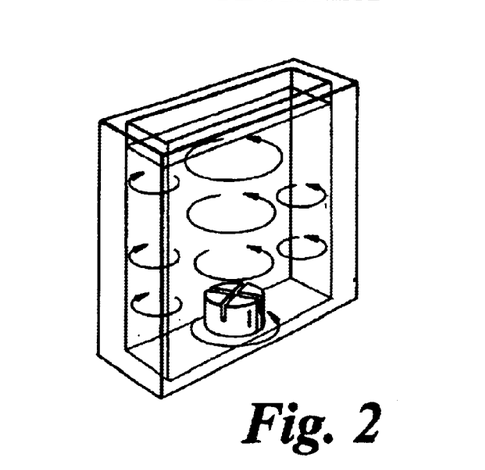
FIG. 2 is a prior art small volume sample cell with a magnetic flea rotating about a vertical axis.

A number of solutions to this problem have been applied to small volume systems including where a syringe is used to inject the sample directly into the measurement cell and measurements are made before the particles can settle out. Another solution to the problem of settling out is the use of a rotating stirrer bead (flea) on the base of a narrow sample cuvette (as shown in FIG. 2). This has the problem that only the region of the sample near to the flea is adequately stirred with dead volumes away from the flea receiving only poor agitation. There is also only a very weak agitation in the vertical direction with such motion only arising from the interactions of the fluid with the walls of the cuvette. This arrangement can also result in stratification of the particles within the cuvette with coarse materials being more concentrated in the lower half of the cell, for example. Additionally the flea is optimised to operate in a circular beaker not a cuvette of narrow rectangular cross-section. Therefore an excessively long light path would need to be used if the cuvette were to be optimised for the use of a flea.

Figure 3:
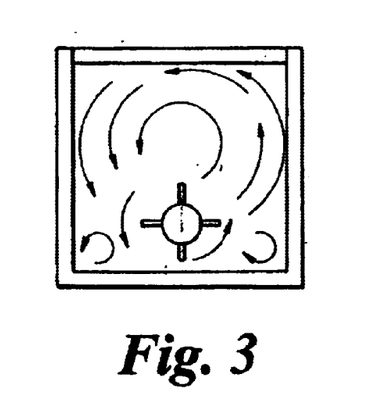
FIG. 3 is a prior art small volume sample cell with a paddle rotating about a horizontal axis.

One proposed alternative method of maintaining the suspension of particles is the use of a horizontally rotating paddle in a cuvette (as shown in FIG. 3). This system does have disadvantages associated with it including regions where there is poor agitation, typically in the corners of the cell where deposits of coarse particles can form. A further problem is that the particles follow preferred trajectories that are dictated by their particle size. This can result in the formation of strata within the cell, the strata containing different particle size populations by virtue of the preferred trajectories and thus skewing measurement results. Also at higher speeds of rotation of the paddle the system acts as a centrifuge throwing larger particles out to the sides of the cell and depleting those particles from the central volume, where measurements are usually taken, which again skews measurement results.

The use of a manual pre-stir and measurement after particles have settled into Brownian motion and sedimentation is known, however, this is only feasible with very fine particles as the time taken for a measurement is typically longer than the time taken for the particles to settle in such a system.

Many systems use an ultrasonic transducer in order to disperse the particles within the suspension and also a degree of agitation of the particles occurs due to the sonication. There are two usual forms of ultrasonic transducer, the first being a limpet style of transducer which is attached to the outer surface of the tank wherein the suspension is stored, the second type of ultrasonic transducer is an in-line probe which is in effect immersed in the solution.

The use of a limpet style transducer attached to the sample tank in a large volume system typically does not give a high degree of coupling of the sonication energy into the sample. This arrangement is inefficient as only a small amount of displacement is caused for a large energy input.

Figure 4:
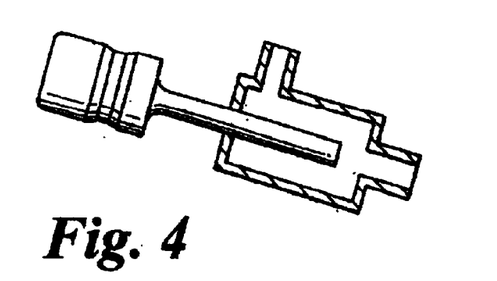
FIG. 4 is an in-line ultrasonic transducer of the prior art.

The in-line probe type of transducer (see for example FIG. 4) yields excellent coupling of the sonication energy into the sample. However, there are regions around the probe and its entry point into the flow path, which will not be well flushed with liquid and could present a potential source of particle trapping and therefore biasing of the system. There is also the problem of large potential power losses at the seal between the internal and external parts of the probe.

Also as the transducer only covers a small area of the tank in a large volume system it is possible that a large proportion of the sample may bypass the ultrasonic transducer and thereby avoid being agitated.

The majority of sample handling systems have a tank in which a large volume of sample, i.e. particulate matter and dispersant, are stored. As it is difficult to achieve uniform agitation of particles with any appreciable density or size variation there is a tendency to size separation within the tank. As a result of this separation it is difficult to find a level at which the outlet to the pump is free of any bias. The sample return from the measurement cell can also significantly bias a tank system, as it is possible that coarse material "short circuit" the tank and pass straight back into the pump inlet thus the material passing through the measurement cell will be unrepresentative of the true bulk nature of the sample and appear overly coarse.

The sample drain also presents a number of problems as current drains utilise the fact that the pump cavity floor is typically the lowest part of the flow path and thus the pump cavity floor is made so that it can drop away and the sample can drain from this point. Provided that the actuator closing the drain is sufficiently powerful then the floor can be clamped without there being any additional gaps to trap particles or dead volumes. This does however rely on the fact that the pump cavity is below the level of the tank and as there is a desire to minimise volume, storage tanks will be reduced in size or ideally eliminated in these small volume systems, this may not be possible.

It is an object of the present invention to ameliorate at least one of the aforementioned disadvantages.

It is a preferred object of the invention to provide a sample handling system in which the overall volume of the system is reduced.

It is a preferred object of the invention to provide a sample handling system in which the number of sites at which deposition of particles in the sample can occur is minimised.

It is a preferred object of the invention to provide a sample handling system in which particle reclamation is maximised when the sample is drained from the system.

It is a preferred object of the invention to provide a sample handling system in which the portion of the sample presented in a measurement zone at any time is substantially representative of the sample as a whole.

It is a preferred object of the invention to provide a sample handling system in which the efficiency of the ultrasonic transducer is improved in order to reduce heating of the system and to ensure that substantially all of the particles pass over an ultrasonically active region thereby enhancing the dispersion and de-aggglomeration of the particles.

Other objects, features and benefits of the invention will be understood from the description herein.

Thus, according to the broadest aspect of the invention there is provided a sample handling system, preferably a small volume system, in which skewing or distortion of measurements is reduced or eliminated by improvements to one or more features of the system such as flow paths, mixing and suspension of the sample.

As used herein the term 'small volume' is intended to define a system in which the total volume is 100 ml or less, preferably 80 ml or less and more preferably 50 ml or less and most preferably 30 ml or less.

According to a first aspect of the present invention there is provided a particle suspension handling system comprising:

- a dispersion unit;
- a transport element,
- a cell;
- said dispersion unit including at least one wall;
- a transducer being mounted upon said at least one wall, externally of said dispersion unit and being arranged, in use, to transfer energy into the suspension; and
- said transport element being located within said dispersion unit and being arranged, in use, to recirculate the suspension about a flow path including said dispersion unit and said cell.

The system may have a total volume of 80 ml or less. The transducer may be an ultrasonic transducer, The transport element may be arranged to remove cavitation bubbles from the at least one wall, in use. The transducer may extend over substantially all of the at least one wall. The transport element may be an impeller. Substantially all of the suspension may flow over the at least one wall, in use.

Particle characterisation apparatus having a detector arranged to detect signals dependant upon the characterisations of particles in a test sample, and a volume particle suspension handling systems according to the first aspect of the present invention.

Desirably the dispersion unit is in the form of a chamber. The chamber may form a pump chamber and may have an impeller mounted therein. The impeller may have blades, which may be equi-angularly spaced The base of the chamber may be a flat surface forming a diaphragm. Preferably the combined volume of the inlet means and dispersion unit is less than 50 ml, more preferably less than 30 ml, very preferably less than 25 ml or optimally less than 20 ml.

Additionally, the dispersion unit may include an ultrasound unit. The ultrasound unit may be attached to the diaphragm, or alternatively it may form the base of the pump chamber. The ultrasound unit may extend over substantially all of the base area of the pump chamber. In use, the ultrasound unit may cause cavitation across the base of the pump chamber. Preferably the impeller clears the cavitation bubbles from the base of the pump chamber thereby increasing the degree of coupling of the ultrasonic energy with the sample. Ideally substantially all of the sample flows past the ultrasound unit during its cycle around the sample handling system. The ultrasound unit need only be used periodically. The ultrasound unit may cause the de-agglomeration of aggregates of small particles.

According to a second aspect of the present invention there is provided a particle suspension handling system comprising:

- a dispersion unit;
- a cell;
- an outlet region;
- the outlet region including first and second valve members, said first and second members being configured, in a first arrangement, wherein said members are spaced apart such that the space between said members is a discharge opening via which a fluid or the suspension exits the system in use;
- the members being configured, in a second arrangement, wherein the members abut and a flow path of substantially constant cross-section is provided about the outlet region.

The system may have a total volume of 80 ml or less. A gallery in the second member may be arranged to place an input opening and an output opening of the first member in said flow path when the members are in their second configuration. A biasing element may be arranged to retain the first and second members in abutment, in use. The biasing element may be a spring. An actuation element may be arranged to relatively displace the first and second members between said first and second configurations. The actuation element may include a servomotor. A biasing element may be arranged to retain the first and second members in abutment, in use, and an actuation element may be arranged to relatively displace the first and second members between said first and second configurations, the bias of the biasing element may be sufficient to retain the members in their second configuration should the actuation element fail. The biasing element may be a spring and the actuation element may include a servomotor. A face of the second member, opposite a face of the first member, may be spaced apart from the first member, in the first configuration, such that a fluid exiting an outlet of the first member may flow over substantially all of the face of the second member, in use. There may be provided a collection chamber adjacent said discharge opening which may be arranged to capture the fluid or suspension which exits the system in the first configuration, in use.

Particle characterisation apparatus having a detector arranged to detect signals dependant upon the characterisations of particles in a test sample and having a small volume particle suspension handling system according to the second aspect of the present invention.

The outlet region has open and closed configurations. In the closed configuration the outlet region may constitute an unbroken flow path within the sample handling system thereby reducing the number of possible sites for deposition of a particulate carried in the sample. The outlet region may have input and output and discharge openings. The input and output openings may form part of an unbroken flow path when the outlet region are in the closed configuration. Preferably the discharge opening receives the majority of the dispersant when the outlet region are in the open configuration. The outlet region may be formed from first and second members and a drain region. Preferably the first and second members are in mutual abutment in the closed configuration. Ideally the first and second members are spaced apart in the open configuration. The space between the first and second members may define the discharge opening. Preferably the drain region is adjacent to the discharge opening. The first member may be a manifold having both input and output openings therein and the second member may be a block with a gallery therein which conjoins the input and output openings in the closed configuration and may be semi-elliptical in cross-section. Alternatively the first and second members may be an O ring and a tube respectively. Another alternative is that both first and second members may be tubes. A biasing element may retain the first and second members in abutment. The biasing element may be a coiled spring or other suitable type of spring, for example a leaf spring. The first and second members may be moved from abutment by an actuation element. The actuation mechanism may be electromechanical or alternatively may be manual. Preferably the bias of the biasing element is such that should the actuation element fail the first and second members will be positively retained in mutual abutment. The drain region may substantially surround the first and second members. Preferably the face of the second member is displaced from the first member when they are in the open configuration, such that when the system is flushed with clean dispersant the region of the face around the input and output opening is washed by the clean dispersant.

According to a third aspect of the present invention there is provided a particle suspension handling system comprising:

a dispersion unit;

a transport element;

a cell;

said dispersion unit including at least one wall;

an ultrasonic transducer being mounted upon said at least one wall, externally of said dispersion unit and being arranged, in use, to transfer ultrasonic energy into the suspension;

said transport element being located within said dispersion unit and being arranged, in use, to recirculate the suspension about a flow path including said dispersion unit and said cell; and the total volume of the system being 80 ml or less.

According to a fourth aspect of the present invention there is provided a particle suspension handling system comprising:

a dispersion unit;

a cell;

an outlet region;

the outlet region including first and second valve members, said first and second members being configured, in a first arrangement, wherein said members are spaced apart such that the space between said members is a discharge opening via which a fluid or the suspension exits the system, in use;

the members being configured, in a second arrangement, wherein the members abut and a flow path of substantially constant cross-section is provided about the outlet region;

a face of the second member, opposite a face of the first member, is spaced apart from the first member, in the first configuration, such that a fluid exiting an outlet of the first member flows over substantially all of the face of the second member, in use; and a gallery in the second member is arranged to place an input opening and an output opening of the first member in said flow path when the members are in their second configuration; and the system has a total volume of 80 ml or less.

According to another aspect of the present invention there is provided a method of characterising a property of a fluid or a dispersion comprising the steps of:

I. Using a small volume sample handling system according to any of the other aspects of the present invention to maintain the fluid or dispersion in motion;

II. Passing radiation through a window in a measurement cell of the sample handling system;

III. Collecting radiation affected by the fluid or dispersion;

IV. Analysing the radiation affected by the fluid or dispersion in order to characterise a property of the fluid or dispersion.

Preferably the dispersion comprises a dispersant and a particulate. The particulate may be a pharmaceutical compound. Desirably the radiation is monochromatic. The radiation may be provided by a laser and will therefore be both monochromatic and coherent. The radiation affected by the fluid or dispersion may have suffered any or all of absorption, scattering or attenuation. Ideally radiation affected by a dispersion is analysed to characterise a particle size distribution within the dispersion.

According to yet another aspect of the invention there is provided a small volume sample handling system comprising an integrally formed inlet means and dispersion means, a measurement cell and outlet means, the inlet means, dispersion means, measurement cell and outlet means being interconnected so as to provide a circulatory flow path; the dispersion means also acting as a pump means.

According to a further aspect of the present invention there is provided a small volume sample handling system comprising an inlet means, a dispersion means, a measurement cell and outlet means all being interconnected so as to provide a circulatory flow path, the measurement cell having a flowpath therethrough and a window therein, the window forming a first part of a wall of the flowpath being flush with a second part of the wall of the flowpath.

According to another aspect of the present invention there is provided a small volume sample handling system comprising an inlet means, a dispersion means, a measurement cell, and outlet means all being interconnected so as to provide a circulatory flowpath, the outlet means having a bore of constant cross-sectional area therethrough.

According to a still further aspect of the present invention there is provided a sample handling system comprising an inlet means, a dispersion, a cell and outlet means.

The invention will now be described by way of example, with reference to the accompanying drawings in which.

Figure 5:
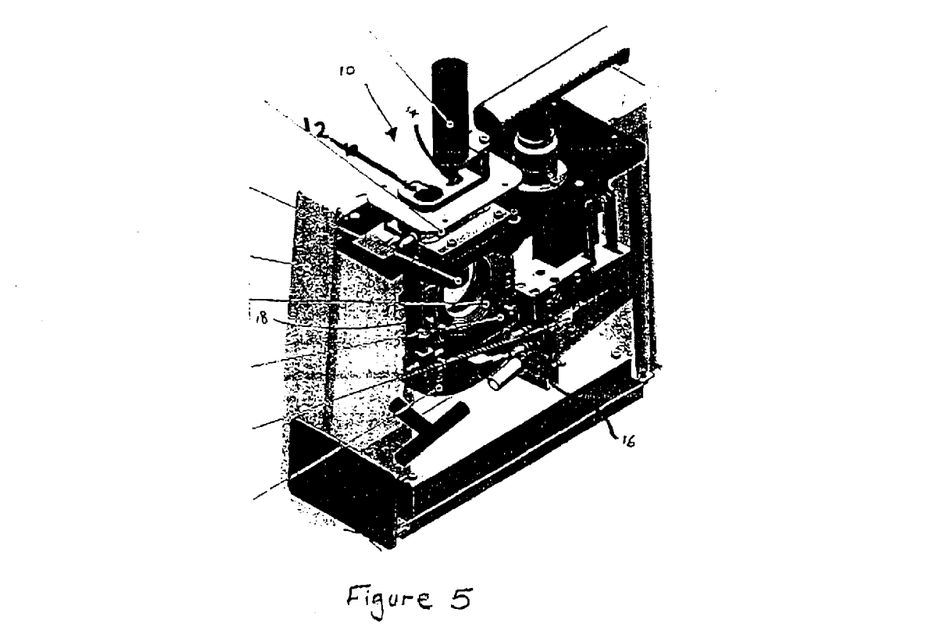
FIG. 5 is a sample handling system according to the present invention.

A small volume sample handling system 10 comprises an inlet arrangement 12, a pump and dispersion unit 14, an outlet port 16 and a measurement cell 18. Typically the system 10 will have a total volume of less than 80 ml, but it can be as low as 20 ml.

Figure 6:
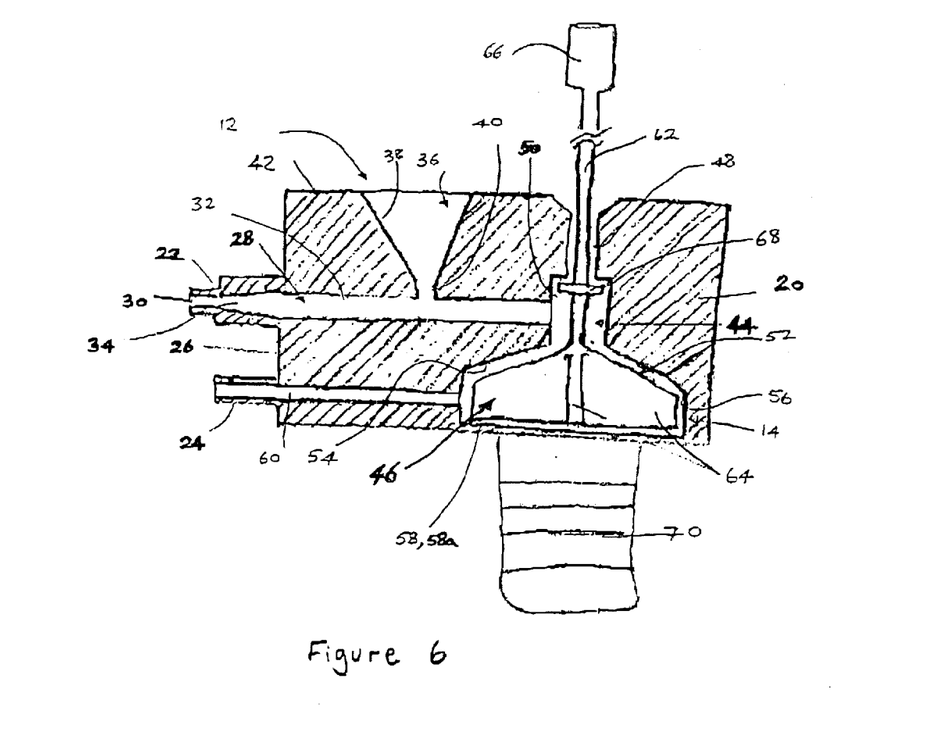
FIG. 6 is an inlet arrangement and a dispersion unit according to the present invention.

Referring now to FIG. 6, this shows an embodiment of an inlet arrangement 12 and the dispersion unit 14 of the sample handling system 10.

The inlet arrangement 12 and pump and dispersion unit 14 are housed within a substantially rectangular body 20 having first and second projections 22, 24 of circular cross-section projecting at right angles to an external surface 26 thereof.

A horizontal cross-drilling 28 enters the body 20 through the first projection 22. The cross-drilling 28 has a narrow entry section 30 which is in communication with a wide body section 32 via an inwardly widening frusto-conical section 34.

An access port 36 has an upper frusto-conical hopper 38 and a lower plain hopper and a lower plain cylindrical narrow chimney 40 (typically 0.1–0.2 ml in volume) and is formed in a second surface 42 of the body 20, the second surface 42 being at right angles to the first surface 26. The chimney 40 intersects the cross-drilling 28 at right angles thereto, thus placing the hopper 38 in communication with the cross-drilling 28. The cross-drilling 28 terminates internally of the body 20 upon entering the dispersion unit 14.

The sample enters the cross-drilling 28 via the entry section 30 and has its flow speed reduced as it passes along the widening frusto-conical section 34 and flows through the body section 32.

Particulate matter is loaded into the hopper 38 and enters the flow path via the chimney 40. Typically the sample resides at a level which encroaches slightly into the chimney 40, this prevents the entrainment of air into the system. This is important as air bubbles will scatter laser light and produce spurious results in particle size characterisation experiments. The chimney 40 has the added advantage of reducing eddy currents within the sample upon the introduction of the particulate matter. The chimney 40 also reduces eddies in the hopper 38 if filled to that level, and reduces deposition of particles on the walls of the hopper 38.

The dispersion unit 14 includes a pump chamber 44 and an impeller 46 which drives the fluid about the system 10. A narrow pump shaft tube 48 of circular cross-section opens through the surface 42 and is in communication with the chamber 44 via a cylindrical neck 50. The cross-drilling 28 opens into the neck 50 at right angles to the longitudinal axes thereof. The neck 50 opens into an impeller housing 52 on the opposite side of the cross-drilling 28 to the pump shaft tube 48.

The impeller housing has an outwardly radially extending gently sloping frusto-conical surface 54 which terminates in a plain cylindrical surface 56 which is parallel to the surface 26. The chamber 44 has a flat basal wall 58, an annular edge region of which is thin enough (typically 0.7–1 mm) to form, in use, a diaphragm 58a. A second cross-drilling 60 exits the chamber 44 through the surface 56 and extends parallel to the cross-drilling 28 opening outwardly through the projection 24. The cross drilling 60 is arranged so that it exits tangentially from the surface 56.

The cross-drilling 28, the pump chamber 44 and a second cross-drilling 60 thereby form a flow path for the sample around the inlet arrangement 12 and the dispersion unit 14, a typical flow rate about this system is approximately 2 liters/min.

The impeller 46 has a drive shaft 62 and four impeller blades 64, although any suitable number of blades may be used. The drive shaft 62 is connected to a motor 66, preferably a brushless motor with bearing seals, externally of the body 20 and passes through the pump shaft tube 48 and neck 50 with no sliding seals. The drive shaft 62 has an annular baffle 68 thereabout which has a larger diameter than the pump shaft tube 48, between the level of the cross-drilling 28 and the junction of the pump shaft tube 48 with the neck 50. It should be noted that the baffle 68 need not have a diameter which is greater than that of the pump shaft tube 48. The impeller blades 64 are attached to, or formed integrally, with the drive shaft 62 and are equi-angularly spaced thereabout. Each blade 64 has a cross-sectional shape which is congruent with, but slightly smaller than, that of the internal surface of the impeller housing 52, Although two pairs of blades 64 are shown, it should be noted that any convenient number of impeller blades can be used.

A motor 66 drives the impeller 46 via drive shaft 62, as there are no sliding seals about the draft shaft 62 this minimises the opportunity for the milling and break up of the particles by the drive shaft 62. The pumping rate and flow speed achievable using this arrangement are equivalent to those of a large volume system, i.e. 2 liters/min.

A piezoelectric ultrasonic drive unit 70 is attached externally of the basal wall 58 of the pump chamber 44 but does not extend over the diaphragm 58a. In use, the ultrasonic drive unit 70 causes cavitation in the sample at the internal surface of the diaphragm 58a.

The edges of the impeller blades 64, which are parallel to the diaphragm 58a are slightly space apart therefrom. The edges of the blades 64 may be inclined relative to the diaphragm 58a to aid in the removal of bubbles therefrom. Upon the actuation of the ultrasonic drive unit 70 the cavitation bubbles formed at the diaphragm 58a are cleared from diaphragm surface 58a by the action of the impeller 46, thereby enhancing the coupling of the ultrasonic energy into the sample. This enables the ultrasonic drive unit 70 to be used less frequently or at lower power than in conventional systems which results in reduced heating of the fluid with the consequence that variations in the refractive index of the fluid, which can cause anomalous experimental results, are less A further consequence of this only periodic use of the ultrasonic drive unit 70 is reduced cavitation damage to the impeller 46 and the impeller housing 52.

In this arrangement, the impeller housing 52 has a small volume and the ultrasonic drive unit 70 extends over the majority of the area of the basal wall 58 with the consequence that substantially all of the fluid and hence the particles therein will pass the ultrasonic drive unit 70 during the cycle round the system 10. This reduces the possibility of particles "short circuiting" the ultrasonic drive unit 70.

The ultrasonication of the sample breaks up large aggregates of small particles which would otherwise bias experimental results.

The external mounting of the ultrasonic drive unit 70 removes the possibility of particles becoming resident upon surfaces of an internally mounted ultrasonic dispersion unit which would also serve to disrupt the flow path of the fluid around the system 10.

The integration of the inlet arrangement 12, pump chamber 44 and the ultrasonic drive unit 70 removes the necessity for a storage tank, as in large volume systems. The storage tank is one of the major sites where particles settle out from dispersion and thus by eliminating the tank a major source of bias is removed from the system 10 when it is used in laser scattering particle characterision experiments.

Figure 7:
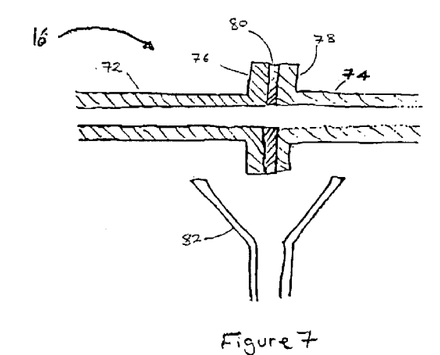
FIG. 7 is a schematic representation of first embodiment of an outlet port, in a closed configuration, according to the present invention.
Figure 8:
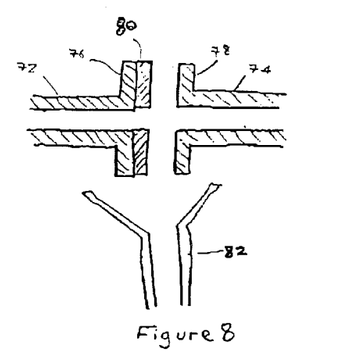
FIG. 8 is a schematic representation of the first embodiment of the outlet port of FIG. 7, in an open configuration.

Referring now to FIGS. 7 and 8 in which is schematically shown a first embodiment of the outlet port 16 comprising first and second pipes 72, 74 having circular cross-sections. Each of the pipes has a respective annular flange 76, 78 extending radially outward at ends adjacent to each other. The first pipe has an annular seal 80 having the same inner and outer radii as the flange 76 attached thereto, although only the inner radii need be equal. A drain region 82 is provided underneath the annular flange 78 on the second pipe 74.

In use, when the outlet port 16 is in a closed configuration, i.e. fluid flows around the system 10 and is not discharged, the seal 80 is held in abutment with the annular flange 78 by a biasing means (not shown). The two pipes 72, 74 present a continuous flow pattern to the sample in this configuration. When the outlet port 16 is in an open configuration the biasing means on the first pipe 72 are released, reversed or overcome so as to distance the annular seal 80 from the annular flange 78 thereby allowing the discharge of the fluid flowing around the system 10 into the drain region 82.

It will be appreciated that it need not be the first pipe 72 which is biased but it could be the second pipe 74 or both pipes 72, 74. It will be further appreciated that it could be either or both pipes which move relative to the position of the drain region 82 in order to effect the discharge of the sample.

Although shown with a seal 80 it is envisaged that the annular flanges 76, 78 could be held in direct mutual abutment in order to effect the sealing of the outlet port 16. A seal would then be provided projecting from the face of one of the flanges 76, 78.

Figures 9, 11:
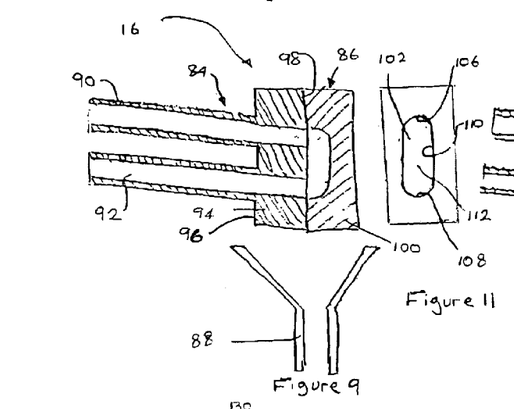
FIG. 9 is a schematic representation of a second embodiment of an outlet port, in a closed configuration, according to the present invention.
FIG. 11 is a schematic representation of a flow chamber of the outlet port of FIGS. 9 and 10.
Figure 10:
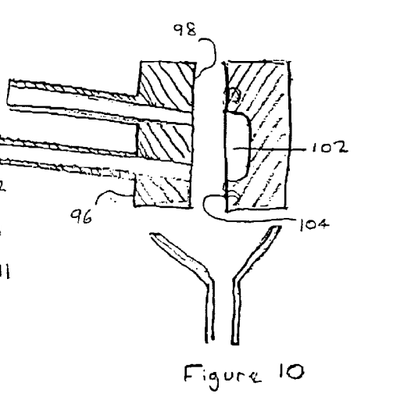
FIG. 10 is a schematic representation of the second embodiment of the outlet port of FIG. 9, in an open configuration.
Figure 12:
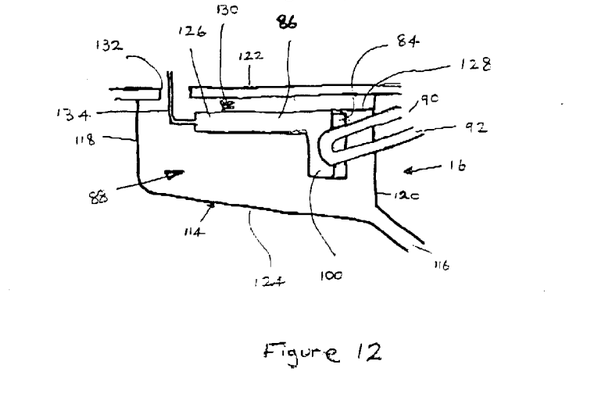
FIG. 12 is a sectional view of the second embodiment of the outlet port of FIGS. 9 and 10.

A second, and preferred embodiment of the outlet port 16 is shown schematically in FIGS. 9 and 10 and 11 and in detail in FIG. 12.

The outlet port 16 comprises a manifold 84, a flow chamber 86 and a drain region 88.

The manifold 84 includes an inlet pipe 90 and an outlet pipe 92 which are formed integrally with a substantially solid body part 94 which is rectangular in cross-section. The inlet and outlet pipes, 90, 92 project from a first face 96 of the body part 94 and both are inclined at the same angle thereto. The respective walls of the pipes, 90, 92 pass through the body part 94 and exit from a second face 98 which is opposite the first face 96.

The flow chamber 86 comprises a solid block 100 of rectangular cross-section having a recess 102 which extends over a distance equal to the distance between the largest separation of the walls of the pipes 90, 92.

The recess 102 has first and second quadrispheres 106, 108 of equal radii at the ends thereof which are joined by an elongate body section 110 having a curved inner surface 112 with a radius of curvature equal to that of the radii of the quadrispheres 106, 108, so as to define a semi-ellipsoidal surface 114 of the recess.

In use, in a closed configuration, the manifold 84 and the flow chamber 86 are sealingly held with the respective faces 98, 104 in mutual abutment, typically by a biasing means (not shown), with no sliding seals only direct face seals. The pipes 90, 92 and recess 102 are aligned so as to define a flow path thereabout such that fluid can flow inlet pipe through the recess 102 and out of the outlet pipe 92. The radii of curvature of the quadrispheres 106, 108 and the elongate body part 110 are such to define a smooth flow path of substantially constant cross-sectional area around the manifold 84 and the flow chamber 86 with no dead volume.

The lack of dead volumes, projections and recesses in the flow path around the manifold 84 and the flow chamber 86 greatly reduce, or ideally eliminate, sites at which particle trapping can occur. Thus, the provision of a smooth flow path of constant cross section alleviates, as identified earlier, a significant experimental bias.

In the open configuration the biasing of either of the manifold 84 or the flow chamber 86 is reversed overcome, or unbiased in this case it is the flow chamber 86 which is biased. This spaces the flow chamber 86 slightly from the manifold 84 thus allowing the discharge of fluid entering the outlet port 16 via the inlet pipe 90 into the drain region 88.

Discharging clean, or substantially clean, dispersant from the inlet pipe 90 washes the face 104 and the recess 102 of the flow chamber 86 thereby improving particle reclamation and reducing the risk of cross-contamination between subsequent samples. This also serves to reduce particle contamination at the interface between the face 104 and the seals thereby reducing wear on the seals.

Although shown with the faces 98, 104, being sealingly abutted it is envisaged that there may be a seal, such as an O ring or similar, therebetween despite the fact that the presence of a seal presents an additional particle trap. In the case of direct abutment of the faces there is very little wear on the face seals. If an O-ring is used it sits in a groove and the metal faces are brought in to abutment so as to allow no gap therebetween.

Referring now to FIG. 12 this illustrates the preferred embodiment of the outlet port in-situ in the sample handling system 10. The drain region 88 takes the form of a tray 114 enclosed by side panels (not shown) with an outlet in the form of a tube 116. The tray 114 has a rear wall 118 and a front wall 120 both of which depend perpendicularly from a plate 122. The front wall extends beyond the termination of the rear wall 118 and an inclined base joins the terminal edges of the rear and the front walls 118, 120. The outlet tube 116 projects from the junction of the front wall 120 and the base 124 thereby placing the interior of the drain region 88 in communication with the exterior.

The pipes 90, 92 pass through, and are fixedly attached to (typically by welds), the front wall 120, The manifold 84 is rigidly held inside drain region 88 by screws (not shown). In this embodiment, the flow chamber 86 is substantially L shaped with block 100 being adjacent the manifold 84 and an arm 126 extending from the block 100 towards the rear wall 118. The flow chamber 86 is retained in position by a leaf spring 128 which passes over the manifold 84 and is fixed to both the front wall 120 and a surface of the arm 126 opposite the plate 122. The leaf spring 128 may be attached to either or both surfaces by a number of fixing means including screws, bolts, welds or adhesive.

The flow chamber 86 is pivotally biased into abutment with the manifold 84 by a helical coiled spring 130 which extends between the plate 122 and the arm 126. The pivot point is on the free portion of the leaf spring 128 between two fixing points. It will be appreciated that any convenient form of biasing means can be used.

The plate 122 has an opening 132 there through which an L shaped actuation member 134 passes through. The actuation member 134 is attached to the opposite end of the arm 126 to the leaf spring 128. An electromechanical actuator such as a servo motor, or a manual actuation device (not shown), is attached to the actuation element.

In use, when the outlet port 16 is in the closed configuration fluid flows into the inlet pipe 90 through the recess 102 and out of the outlet pipe 92 as hereinbefore described.

In order to achieve the open configuration of the outlet port 16 the actuator causes the actuation member 134 to be withdrawn outwardly through the opening 132 against the applied biasing force of the coiled spring 130. This causes the flow chamber 86 to be pivoted away from a manifold 84 thereby creating a space therebetween, Thus, any fluid flowing through the inlet pipe 90 will flow out over the recess 102 and the face 104 of the block 100 and be collected in the tray 114. This cleans any particles from the recess 102 and the face 104 thereby improving the efficiency of particle reclamation.

The inclined base 124 of the tray 114 ensures that any fluid which collects therein drains towards the tube 116. The inclined base 124 aids the reclamation of particulates contained within the sample. The helical coiled spring 130 exerts a biasing force sufficient that should the actuator or actuation member 134 fail with the outlet port 16 in its open configuration the flow chamber 86 will be biased into abutment with the manifold 84 thus closing the outlet port 16 and effectively failing safe.

Accordingly the actuator need only be energised when the outlet port is to be opened thereby conserving energy.

Figure 13:
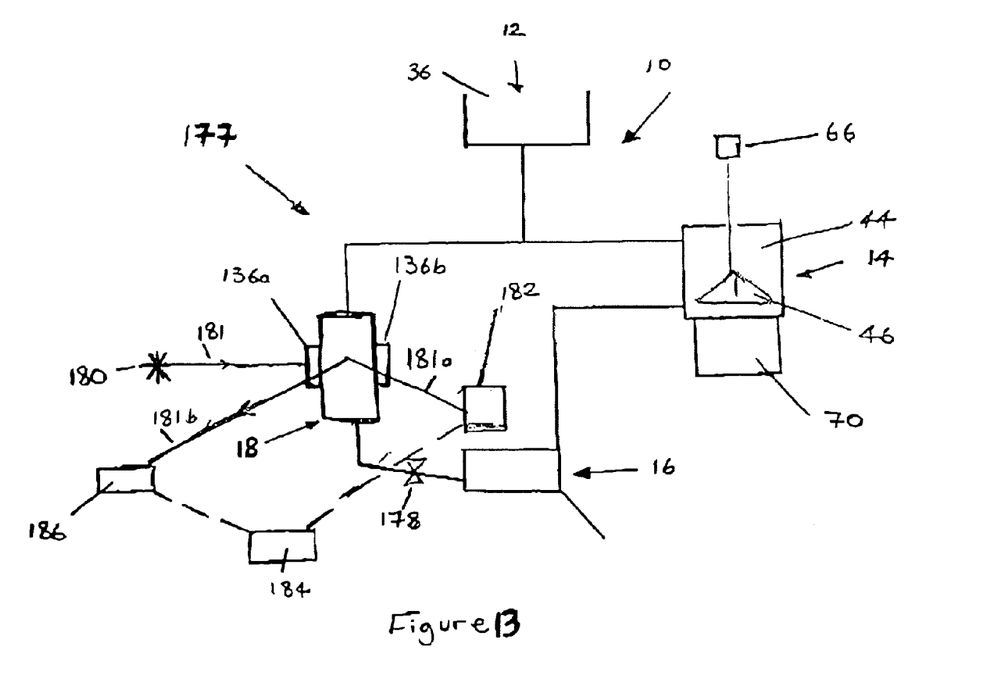
FIG. 13 is a schematic representation of a small volume sample handling system according to the present invention, in use, in a laser scattering particle size characterisation system.

Referring now to FIG. 13 (with reference to FIGS. 5, 6, 9 and 12) this shows, schematically, the small volume sample handling system 10, in use, in a laser scattering particle characterisation apparatus 177.

Initially the apparatus 177 contains no dispersant or sample. Dispersant is introduced into the apparatus 177 via an inlet valve 178 or alternatively via the inlet arrangement 12. The inlet valve 178 is functionally similar to the inlet arrangement 12 in that dispersant is introduced at right angles to the flow paths via a chimney in order to remove any sliding seals which may act as particle traps. The inlet valve 178 has a similar form to the inlet arrangement 12, being a vertically mounted tee junction with the chimney as narrow as possible, typically 0.5 mm. It also has an inlet hopper with a sloping conical surface so as to return any particles to the flow path, should the dispersant enter the hopper.

Once the apparatus 177 is filled with dispersant the dispersion unit 14 is actuated, the motor 66 driving the impeller 46. The impeller 46 pumps the dispersant about the system as follows; via the outlet port 16 and vertically upward through the measurement cell 18, past the access port 36, returning to the pump chamber 44, the flow path about the system 10 being defined by a series of tubes (not shown).

The particulate of interest is placed in the access port 36 from where it enters the flow path via the hopper 38 and chimney 40 and flows around the apparatus 177 following the flow paths hereinbefore described. The dispersant and particulate of interest recirculate around the system 10 to allow multiple laser scattering measurements to be taken of the particulate of interest.

The upward motion of the sample through the measurement cell 18 helps prevent the settlement of larger particles by keeping them in constant motion under an applied pumping force.

A laser light source 180 produces a coherent, monochromatic beam of light 181. The light 181 enters the measurement cell 18 through a first window unit 136a. The particles in the sample scatter the light 181 and a fraction of the scattered light 181a is forward scattered through a second window unit 136b to a forward scatter detector 182. The forward scatter detector 182 converts the intensity of the forward scattered light 181a into either an analogue or a digital signal which is then passed to a computational device 184, for example a PC, which converts the intensity data into a particle size distribution for the sample. Alternatively, the analysis may be performed by the forward scatter detector 182 and displayed on a screen, printout or recorded on a readable medium such as a diskette or CD-Rom.

A further portion of the light 181b will be backscattered through the first window 136a and can be collected by a backscatter detector 186 which can be connected to the computational device 184, or not as discussed earlier.

The large take off angles of the window units 136a, 136b ensures that the amount of light exiting the measurement cell is increased and therefore the amount and quality of information which can be obtained regarding the sample size distribution is consequently increased.

The ultrasonic drive unit 70 can be actuated, either intermittently or constantly, during measurements in order to aid dispersion of the particles in the dispersant and also to break up large aggregates of fine particles.

When sufficient measurements have been made to adequately characterise a sample's size distribution the sample is discharged form the apparatus 177 via the outlet port 16 and the apparatus 177 is flushed with clean dispersant as described hereinbefore.

Whilst the sample handling system 10 has been described in use in a laser scattering particle size characterisation apparatus it will be appreciated that it could be used in many systems in which a recirculating measurement cell is required.

It will be further appreciated that although described with particular reference to a small volume sample handling unit the inventive concepts and features described herein are equally applicable to large volume sample handling systems.

What is claimed is:

1. A particle suspension handling system comprising:
 a dispersion unit;
 a measurement cell;
 an outlet region;
 the outlet region including first and second valve members located distal to the cell, the first and second members being configured, in a first arrangement, wherein said members are spaced apart such that the space between said members is a discharge opening via which a fluid or the suspension exits the system in use;
 the members being configured, in a second arrangement, wherein the members abut and a continuous flow path is provided about the outlet region, the flow path interconnecting the dispersion unit and the cell; and
 wherein a recess in the second member is arranged to place an input opening and an output opening of the first member in said flow path when the members are in their second arrangement.

2. A system according to claim 1 wherein the system has a total volume of 80 ml or less.

3. A system according to claim 1 wherein a biasing element is arranged to retain the first and second members in abutment, in use.

4. A system according to claim 3 wherein the biasing element is a spring.

5. A system according to claim 1 wherein an actuation element is arranged to relatively displace the first and second members between said first and second arrangements.

6. A system according to claim 5 wherein the actuation element includes a servomotor.

7. A system according to claim 1 wherein a biasing element is arranged to retain the first and second members in abutment, in use, and an actuation element is arranged to relatively displace the first and second members between said first and second arrangements, the bias of the biasing element being sufficient to retain the members in their second arrangement should the actuation element fail.

8. A system according to claim 7 wherein the biasing element is a spring and the actuation element includes a servomotor.

9. A system according to claim 1 wherein a face of the second member, opposite a face of the first member, is spaced apart from the first member, in the first arrangement, such that a fluid exiting an outlet of the first member flows over substantially all of the face of the second member, in use.

10. A system according to claim 1 wherein there is provided a collection chamber adjacent said discharge opening arranged to capture the fluid or suspension which exits the system in the first arrangement, in use.

11. A system according to claim 1 wherein said first and second valve members are located below the cell.

12. A system according to claim 1 wherein the flow path is a recirculating flow path through the cell.

13. A system according to claim 1 wherein the flow path has a substantially constant cross-section.

14. Particle characterization apparatus having a detector arranged to detect signals dependent upon the characterizations of particles in a test sample and having a small volume particle suspension handling system comprising:
 a dispersion unit;
 a measurement cell;
 an outlet region;
 the outlet region including first and second valve members located distal to the cell, the first and second members being configured in a first arrangement wherein said members are spaced apart such that the space between said members is a discharge opening via which a fluid or the suspension exits the system in use;
 the members being configured in a second arrangement wherein the members abut and a continuous flow path is provided about the outlet region, the flow path interconnecting the dispersion unit and the cell; and
 wherein a recess in the second member is arranged to place an input opening and an output opening of the first member in said flow path when the members are in the second arrangement.

15. A system according to claim 14 wherein said first and second valve members are located below the cell.

16. A system according to claim 14 wherein the flow path is a recirculating flow path through the cell.

17. A system according to claim 14 wherein the flow path has a substantially constant cross-section.

18. A particle suspension handling system comprising:
 a dispersion unit;
 a measurement cell;
 an outlet region;
 the outlet region including first and second valve members located distal to the cell, the first and second members being configured, in a first arrangement, wherein said members are spaced apart such that the space between said members is a discharge opening via which a fluid or the suspension exits the system, in use;
 the members being configured, in a second arrangement, wherein the members abut and a continuous flow path of is provided about the outlet region, the flow path interconnecting the dispersion unit and the cell;
 a face of the second member, opposite a face of the first member, is spaced apart from the first member, in the first arrangement, such that a fluid exiting an outlet of the first member flows over substantially all of the face of the second member, in use; and
 a recess in the second member is arranged to place an input opening and an output opening of the first member in said flow path when the members are in their second arrangement.

19. A system according to claim 18 wherein the system has a total volume of 80 ml or less.

20. A system according to claim 18 wherein said first and second valve members are located below the cell.

21. A system according to claim 18 the flow path is a recirculating flow path through the cell.

22. A system according to claim 18 wherein the flow path has a substantially constant cross-section.

* * * * *